US010265392B2

(12) United States Patent
Jacobs

(10) Patent No.: US 10,265,392 B2
(45) **Date of Patent: *Apr. 23, 2019**

(54) **VACCINE FOR USE AGAINST SUBCLINICAL *LAWSONIA* INFECTION IN A PIG**

(71) Applicant: Intervet Inc., Madison, NJ (US)

(72) Inventor: Antonius Arnoldus Christiaan Jacobs, Kessel (NL)

(73) Assignee: Intervet Inc., Madison, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/546,361

(22) PCT Filed: Feb. 3, 2016

(86) PCT No.: PCT/EP2016/052239

§ 371 (c)(1),
(2) Date: Jul. 26, 2017

(87) PCT Pub. No.: WO2016/124623

PCT Pub. Date: Aug. 11, 2016

(65) Prior Publication Data

US 2018/0000924 A1 Jan. 4, 2018

(30) Foreign Application Priority Data

Feb. 4, 2015 (EP) .................................... 15153782

(51) Int. Cl.

*A61K 39/00* (2006.01)
*A61K 39/38* (2006.01)
*A01N 63/00* (2006.01)
*A61K 48/00* (2006.01)
*A61K 39/02* (2006.01)

(52) U.S. Cl.

CPC ...... *A61K 39/105* (2013.01); *A61K 2039/521* (2013.01); *A61K 2039/552* (2013.01); *A61K 2039/55566* (2013.01)

(58) Field of Classification Search

CPC .............. A61K 2039/552; A61K 38/00; A61K 39/102; C12N 15/86; C12N 35/74

See application file for complete search history.

(56) References Cited

U.S. PATENT DOCUMENTS

| | | | | |
|---|---|---|---|---|
| 5,885,823 A * | 3/1999 | Knittel | A61K 39/105 | 435/243 |
| 7,022,328 B1 * | 4/2006 | Panaccio | C07K 14/205 | 424/184.1 |
| 7,029,683 B1 * | 4/2006 | Panaccio | A61K 39/105 | 424/184.1 |
| 8,398,970 B2 * | 3/2013 | Deitmer | A61K 31/00 | 424/184.1 |
| 8,398,994 B2 * | 3/2013 | Kroll | A61K 39/105 | 424/234.1 |
| 8,597,662 B2 * | 12/2013 | Jacobs | A61K 39/105 | 424/184.1 |
| 9,636,389 B2 * | 5/2017 | Fachinger | A61K 39/105 | |
| 2008/0063648 A1 * | 3/2008 | Kroll | A61K 39/105 | 424/164.1 |
| 2010/0062021 A1 * | 3/2010 | Winkelman | A61K 39/105 | 424/234.1 |
| 2016/0303218 A1 * | 10/2016 | Jacobs | A61K 39/0241 | |
| 2016/0303219 A1 * | 10/2016 | Drexler | A61K 39/105 | |

FOREIGN PATENT DOCUMENTS

| | | |
|---|---|---|
| WO | WO199720050 A1 | 6/1997 |
| WO | 2009144088 A2 | 3/2009 |
| WO | 2009127684 A1 | 10/2009 |

OTHER PUBLICATIONS

Extended EP search report for 15153782.6 dated May 18, 2015, 4 pages.
International Search Report, dated Mar. 29, 2016.
Riser, L et al, Vaccination of pigs with attenuated Lawsonia intracellularis inducedacute phase protein responses and primed cell-mediated immunitywithout reduction in bacterial shedding after challenge, Vaccine, 2015, pp. 156-162, vol. 33.
Roof, M et al, The Research and Development of Enterisol® Ileitis, European Enterisol® Ileitis Symposium. Barcelona, Oct. 13-15, 2005.
Vanderheijden et al, Prevalence of exposure and infection of Lawsonia intracellularis among slaughter-age pigs, Research in Veterinary Science, 2004, pp. 197-202, vol. 77 No. 3.

* cited by examiner

*Primary Examiner* — Gary B Nickol
*Assistant Examiner* — Lakia J Jackson-Tongue

(57) ABSTRACT

The present invention pertains to a vaccine comprising non live *Lawsonia intracellularis* antigen and a pharmaceutically acceptable carrier for use in a method to reduce in a pig the shedding of *Lawsonia intracellularis* bacteria associated with subclinical infection with *Lawsonia intracellularis*, by systemic administration of the vaccine to the pig.

8 Claims, No Drawings

VACCINE FOR USE AGAINST SUBCLINICAL *LAWSONIA* INFECTION IN A PIG

CROSS-REFERENCE TO RELATED APPLICATIONS

This application is a national stage entry under 35 U.S.C. § 371 of PCT/EP2016/052239 filed on Feb. 3, 2016, which claims priority to EP15153782.6, filed on Feb. 4, 2015. The content of PCT/EP2016/052239 is hereby incorporated by reference in its entirety.

GENERAL FIELD OF THE INVENTION

The present invention pertains to a vaccine for use in a method to reduce in a pig the shedding of *Lawsonia intracellularis* bacteria associated with subclinical infection with *Lawsonia intracellularis.*

BACKGROUND OF THE INVENTION

Proliferative enteropathy, also known as ileitis, is a common enteric disease of post-weaned pigs worldwide, caused by the obligate intracellular bacterium *Lawsonia intracellularis*. The characteristic lesion is a proliferation of immature enterocytes in the ileal intestinal crypts; these cells usually contain the causative bacteria within their apical cytoplasm. At autopsy, histologic lesions can be confirmed as *Lawsonia*-positive by visualization of 1.5-2.5 μm long, vibrioid shaped bacteria especially in enterocytes, but also often within macrophages located in the lamina propria between crypts, and in mesenteric lymph nodes. Clearance of the bacteria from the enterocytes leads to resolution of the associated proliferative lesions, indicating a direct local effect of the bacteria on the crypts (McOrist et al., *Developed and resolving lesions in porcine proliferative enteropathy: possible pathogenetic mechanisms*, Journal of Comparative Pathology, 115, 1996, pp 35-45). The presence of *Lawsonia intracellularis* in these lesions has been demonstrated using PCR, both in animals manifesting disease (i.e. show diarrhea or abnormal red-black tarry faeces, potentially resulting in death) as in animals manifesting only subclinical infection (not showing diarrhoea or abnormal faeces). Clinical cases are usually present in the grower-finisher period; in some older finisher pigs an acute hemorrhagic form has been recorded.

The relationship between *Lawsonia intracellularis* seropositive pigs and the proportion of pigs presenting clinical or subclinical infection has been studied before (Van der Heijden, *Prevalence of exposure and infection of Lawsonia intracellularis among slaughter-age pigs*., Res Vet Sci, December 2004, 77(3), pp 197-202). It appears that some pigs could be carriers, i.e. are infected but present no clinical signs of ileitis. In particular in Europe, animals which are considered to be free of disease, appear to have subclinical infections, as evidenced by remains of the bacteria at slaughter in the intestines. An explanation for the positive results regarding the presence of *Lawsonia intracellularis* bacteria in clinical disease free herds is that those herds have *Lawsonia intracellularis* moving through their finisher groups. Only in certain situations, the *Lawsonia* infection results in clinical problems, including acute haemorrhagic enteropathy cases.

In clinical disease free herds vaccination against *Lawsonia* infection is uncommon. However, since it is known that subclinical infection may lead to a negative impact on average daily weight gain (ADWG) of a pig, some grower-finisher farms use the sole commercial Ileitis vaccine in the market, i.e. ENTERISOL® Ileitis (a *Lawsonia Intracellularis* vaccine comprising an avirulent live culture, available from Boehringer Ingelheim), to combat local infection in the intestines. This vaccine contains live attenuated *Lawsonia intracellularis* bacteria and is administered orally. Indeed, at present it is believed that a local infection of the gut can only be fought by inducing local immunity. This is different for animals which present clinical disease. It has been shown (WO 2009/144088, assigned to Intervet International BV) that those animals can be successfully protected by systemic vaccination with a non-live vaccine. Without being bound to theory, it is believed that the reason for this is that those animals have severe gastro-intestinal lesions that expose the infection to the system, which would explain why a systemic immune response would help to combat the infection. However, when there is only a subclinical infection, corresponding to a minor local infection of the gut, a local immune response including IgA and cellular immunity is believed to be needed to combat the infection. For this one needs a vaccine comprising live bacteria, administered locally. This is confirmed in the paper of Mike Roof called *The Research and Development of Enterisol® Ileitis*, presented at the European Enterisol® Ileitis Symposium, Oct. 13-15, 2005, Barcelona, Spain. On page 2 it is indicated in Table 1.1 that although a killed vaccine administered systemically might induce "Humoral/systemic immunity", it fails to induce both "Mucosal immunity" and "Cell mediated immunity". The latter two being commonly known as needed to combat a local infection of the gut with intracellular pathogens (Ivan Roitt, *Essential Immunology*, seventh edition, 1991, pages 206 "The secretory immune system protects the external mucosal surfaces", 209 "Defence is by cell-mediated immunity" and 210 "Activated macrophages kill intracellular parasites"). In the Mike Roof paper of 2005 it is stated that "Early investigations looking at killed bacterin prototype confirmed . . .that killed vaccines provided no protective response against . . .the colonization of the gut." (page 2, left hand column, second full paragraph).

The live vaccine ENTERISOL® Ileitis is indeed licensed with a claim to reduce loss of weight gain associated with infection, and is used for that purpose. Disadvantages of this vaccine are that it needs to be administered orally, which is not a routine way of vaccinating pigs, and that one has to interrupt use of antimicrobials in the animals for six days (since otherwise the bacteria in the vaccine might be killed). Another disadvantage is that the vaccine is not licensed for the reduction of shedding of the bacteria. Apparently, data used for the marketing authorization did not show a reduction in shedding of the bacteria. A recent publication (Riber et al. in Vaccine 33, 2015, 156-162) confirmed that ENTERISOL® Ileitis provides no protection at all against shedding of *Lawsonia* bacteria after infection. This might indicate that an infection with *Lawsonia intracellularis* in a herd of animals might remain even though all animals are vaccinated and weight gain problems and clinical manifestations are significantly reduced.

OBJECT OF THE INVENTION

It is an object of the invention to provide an improved vaccine that can be used to reduce the shedding of *Lawsonia* intracelluaris bacteria by subclinically infected pigs. It is a further object to provide an improved vaccine that additionally provides a reduction of the negative impact on ADWG associated with the subclinical infection.

SUMMARY OF THE INVENTION

In order to meet the main object of the invention, a pharmaceutical composition as described in the GENERAL FIELD OF THE INVENTION section here above has been devised, wherein this composition comprises non live *Lawsonia intracellularis* antigen and a pharmaceutically acceptable carrier, and is suitable for systemic administration.

Surprisingly, even though non-live *Lawsonia* antigens given systemically (such as the different types of non live *Lawsonia* antigens as described in WO2009/144088) are commonly understood as being unable to induce IgA and cellular immunity, let alone to affect a local immune response in the gut, it was found that such a composition may reduce the shedding of *Lawsonia intracellularis* in subclinically infected pigs substantially, or even completely prevent the shedding from occurring. The reason for this is unclear, The advantages of the new composition versus the live vaccine as known in the art are clear: the new composition can be administered systemically, for example intramuscularly or intradermally, and since it comprises only non-live *Lawsonia* antigens, antimicrobial use does not need to be interrupted.

DEFINITIONS

A vaccine is a constitution that protects against a post vaccination infection with a pathogenic micro-organism, i.e. a constitution that prevents or reduces the infection by the micro-organism, or a disorder that results from the infection, typically by interfering with the micro-organism itself, for example via antibodies, in the vaccinated host. Vaccination thus prevents, or at least diminishes, the level of infection and/or prevents, or at least diminishes, the level of disorder resulting from that infection.

Non live antigen of a wild type bacterium is any substance or compound, other than the live bacterium as such, against which an immunological response is to be elicited, such that the corresponding virulent bacterium or one or more of its virulence factors will be recognized by the host's immune system as a result of this immune response, and are at least partly neutralized. Typical examples of non live antigen of a wild type bacterium are killed whole cell bacteria, subunits of the bacterium such as surface expressed proteins, and toxins. The latter two may or may not be recombinantly expressed. With regard to *Lawsonia intracellularis*, several types of non live antigen are known in the art, and are for example known from WO2009/144088 (killed whole cell), WO2005/070958 (sub-units) and WO97/20050 (killed whole cell).

A pharmaceutically acceptable carrier is a biocompatible medium, viz. a medium that after administration does not induce significant adverse reactions in the subject animal, capable of presenting the antigen to the immune system of the subject animal after administration of the vaccine. Such a carrier can be a liquid containing water and/or any other biocompatible solvent, but can also be a solid such as commonly used to obtain freeze-dried vaccines (based on sugars and/or proteins).

A subclinical infection with *Lawsonia intracellularis* is an infection that is nearly or completely asymptomatic (no signs or symptoms), in particular not showing diarrhoea or abnormal faeces. The subclinically infected animal is thus an asymptomatic carrier of the intestinal bacterium *Lawsonia*

*intracellularis*, but may be associated with reduced weight gain. The existence of the subclinical infection is identified by microbiological culture of the faeces or intestines (the latter after slaughter), or DNA techniques such as polymerase chain reaction thereof.

Systemic administration of an antigen means that the antigen is administered such that it reaches the circulatory system of the body (this system comprising the cardiovascular and lymphatic system), thus affecting the body as a whole rather than a specific locus such as the gastrointestinal tract. Systemic administration can be performed e.g. by administering the antigens into muscle tissue (intramuscular), into the dermis (intradermal), underneath the skin (subcutaneous), underneath the mucosa (submucosal), and in the veins (intravenous).

The finishing period of a pig is the period wherein the pig is between about 10 weeks of age (having a weight of approximately 25-30 kg) and about 28 weeks of age (having a weight of about 110-130 kg). The finishing period is part of the total grower period, i.e. the period between weaning (approximately 3 weeks of age) and 28 weeks of age, the age at which most pigs are slaughtered.

A composition comprising killed whole cell bacteria as antigen comprises antigen derived from the killing of live, whole cell, bacteria. This does not exclude that the bacterial cells are, at least partly, ruptured during the killing process, or that an extract or homogenate of the killed whole cells is actually provided as the antigen in the "vaccine comprising the killed whole cell bacteria" in the sense of the present invention. Killed whole cell *Lawsonia intracellularis* bacteria are for example known from WO2009/144088 and WO97/20050.

EMBODIMENTS

In a first embodiment the method is for preventing shedding of the bacteria. It appears that the current vaccine, although administered systemically is even able to prevent the infection in more than 90%, even up to 99% of the animals. This is very surprising given the fact that the live vaccine ENTERISOL® Ileitis, which can induce a local immune response in the gut, and thus, should be tailored to combat a sub-clinical infection in the gut, is not even able to merely reduce shedding of the *Lawsonia* bacteria.

In a next embodiment the method in addition is for reducing the negative impact on average daily weight gain (ADWG) of the pig associated with the subclinical infection with *Lawsonia intracellularis*. It appeared that the current vaccine is able positively affect the ADWG of subclinically affected pigs. This is a very important parameter for any pig grower, even if the positive difference in weight gain is only small.

In another embodiment the vaccine is administered only once. A single administration of the vaccine has shown to be effective. A second dose of the vaccine, typically administered 2-4 weeks after the first dose, might improve the level of the immune response.

In another embodiment the vaccine is administered when the pig is 3-10 days of age. By vaccinating the pigs at this young age, early protection can be provided, i.e. protection directly post weaning.

In still another embodiment the non live *Lawsonia intracellularis* antigen comprises the carbohydrates that in live *Lawsonia intracellularis* bacteria are in association with the outer cell membrane of these bacteria. These carbohydrates have shown to be able and rise a specific anti-*Lawsonia intracellularis* immune response (see WO 2009/144088).

In yet another embodiment the non live *Lawsonia intracellularis* antigen is antigen purified from a composition comprising killed *Lawsonia intracellularis* bacteria. By purification, non specific bacterial material can be removed from the actual antigen, for example in order to reduce, if present, any site reactions.

In a practical embodiment the non live *Lawsonia intracellularis* antigen is killed whole cell *Lawsonia intracellularis*.

EXAMPLES

Study 1

Design of Study 1

The study was carried out in a Dutch herd with a *Lawsonia intracellularis* (LI) infection in older finishing pigs and breeding gilts. The study followed a randomised, controlled and blinded design.

One-hundred-and-fifty-eight piglets of 3-10 days of age (most of them being 3-5 days of age) were assigned randomly, within litters, to the test or control group. The piglets in the test group were vaccinated with in inactivated *Lawsonia* bacterin vaccine in an oil in water emulsion (see WO 2009/144088, Example 3) at admission and again 3 weeks later. The piglets in the control group received a placebo injection (emulsion without antigen) at the same days. No antibiotic group medication that was effective against LI (e.g. tylosin, lincomycin, tiamulin, tetracyclins) was allowed in the study animals. After weaning, i.e. in the nursery and finishing phase, the piglets of the test and control group were kept together. Further, during nursery and fattening non-experimental pigs were housed in the same rooms but in different pens as the experimental animals.

The piglets were routinely checked for local and systemic reactions at 4 hours, 1 day, 3 days, 1 week and 2 weeks after each vaccination.

From all pigs faeces samples were taken at one- or bi-weekly intervals during the period of expected exposure to a filed infection. Per treatment group, the faeces samples of ten animals were pooled and analysed for presence of LI bacteria by qPCR (hereafter also referred to as "PCR"). If a pooled faeces sample indicated presence of bacteria, the original samples from that pool were analysed individually. As soon as the first samples became positive, individual faeces samples were tested. At first vaccination, 10, 16 and 21-23 weeks after first vaccination, all animals were weighed.

Results of Study 1

During the study, a *Lawsonia* infection went through the herd as evidenced by PCR data on faeces (see below). Since none of the animals, except for one animal in the control group had any clinical symptoms, the group was affected by a subclinical infection resulting from a field exposure to of the (wild type) bacterium.

Bacterial Load in Faeces

The mean PCR-results are given in Table 1, number of positive animals and mean concentration of LI-DNA are given in Table 2.

From week 13 onwards in a number of control animals, DNA from LI was found. The percentage of control animals with positive faecal samples gradually increased from zero at 12 weeks after first vaccination via 2-8% at week 13-15 up to around 18% at week 16-18, after which it decreased down to 0% after week 20.

TABLE 1

Shedding of LI in the faeces (qPCR)

| | Positive animals | | Duration positivity (weeks) | |
|---|---|---|---|---|
| Group | number | % | mean | range |
| Controls | 31 | 41.3 | 1.65 | 1-5 |
| Vaccinated | 1 | 1.4 | 1.00 | |

In the test (vaccine) group only a single PCR positive faeces sample was found at one collection day for a single animal (1 out of 72 pigs positive, i.e. 1.4%). In the Control group 31 out of 75 animals had at least one PCR positive faeces sample (41.3%). The difference between the groups was statistically significant (Fisher's exact test: p-value <0.001).

TABLE 2

Number of animals with LI positive samples (and percentage) and mean concentration of LI in the positive fecal samples, by vaccination group and week after first vaccination.

| week after 1st | positive samples | | pg DNA/5 μl positive sample (Mean ± SD) | |
|---|---|---|---|---|
| vaccination | Controls | Vaccine | Controls | Vaccine |
| 12 | 0 (0%) | 0 (0%) | | |
| 13 | 2 (2.7%) | 0 (0%) | 138 ± 83 | |
| 14 | 6 (8.0%) | 0 (0%) | 290 ± 396 | |
| 15 | 2 (2.7%) | 0 (0%) | 314 ± 19 | |
| 16 | 14 (18.7%) | 1 (1.4%) | 1262 ± 2458 | 119 |
| 17 | 14 (19.7%) | 0 (0%) | 885 ± 833 | |
| 18 | 9 (17.6%) | 0 (0%) | 1627 ± 3680 | |
| 19 | 3 (5.7%) | 0 (0%) | 1387 ± 1278 | |
| 20 | 1 (3.0%) | 0 (0%) | 98 | |
| 21 | 0 (0%) | 0 (0%) | | |
| 22 | 0 (0%) | 0 (0%) | | |
| 23 | 0 (0%) | 0 (0%) | | |

Body Weight Gain

Body weights and average daily weight gain are summarized in the Tables 3 and 4 below. ADWG is considered to be a relevant parameter that is often used to measure efficacy of *Lawsonia* vaccines. However, this parameter is non-specific as it is influenced by several different conditions (secondary infections, climate, feed, etc.). The preliminary calculated sample size to obtain statistical significant (p<0.05) values at an ADWG difference of 25 grams per day would need to be about 300 animals per group. For efficiency reasons, the groups actually used were made considerably smaller. In this pilot study group sizes were only 78 and 80 animals. So even if the difference in ADWG would be about 25 grams per day, the resulting p value was estimated to be above 0.05 in any case.

TABLE 3

Mean bodyweight (kg, ± SD), by vaccination group and period.

| | Control | Vaccine |
|---|---|---|
| Admission (3-10 days) | 1.4 ± 0.3 (n = 76) | 1.5 ± 0.3 (n = 80) |
| At transfer to finishing (10 weeks) | 27.7 ± 4.8 (n = 74) | 28.5 ± 4.1 (n = 73) |
| Third weighing (±16 weeks of age) | 64.0 ± 9.2 (n = 73) | 65.6 ± 9.1 (n = 71) |
| Last weighing (18-24 weeks of age) | 89.4 ± 16.8 (n = 72) | 92.3 ± 17.0 (n = 71) |

The treatment group comparison for the average daily weight gain during the finishing phase (see below) led to, as expected, no statistically significant difference (p-value 0.2042). If corrected for baseline values, the vaccinated group showed on average 21.4 grams per day higher daily weight gain in the finishing period than the control group, with a 90% confidence interval ranging from 6.4 grams per day lower to 49.2 grams per day higher. An average difference of 21.4 grams per day on itself is a substantial difference in ADWG. The Least Squares Means (LSMs) for the average daily weight gains of the two groups were 881 grams per day for the vaccinated group and 860 grams per day for the control group. These LSMs do fit the group comparison by ANCOVA but are slightly different from the ordinary means from Table 3 as they are corrected for the small differences in the covariate 'weight at vaccination' between groups.

TABLE 4

Mean average daily weight gain in grams*, by vaccination group and period.

| | LSM ± SEM | 90% confidence int. | n pigs |
|---|---|---|---|
| Finishing period | | | |
| Control | 859.9 ± 14.5 | 835.7-884.2 | 72 |
| Vaccine | 881.3 ± 14.6 | 856.8-905.9 | 71 |
| Control-Vaccine | −21.4 ± 16.8 | −49.2-6.4 | |
| Overall | | | |
| Control | 621.6 ± 10.1 | 604.6-638.5 | 72 |
| Vaccine | 634.0 ± 10.2 | 616.9-651.2 | 71 |
| Control-Vaccine | −12.4 ± 11.5 | −31.5-6.6 | |

*Mean ADWG adjusted for litter, batch and weight at admission ± standard error of the mean (SEM) and 90% confidence interval.

The p-value for the treatment effect on overall average daily weight gain was 0.2804. If corrected for baseline values, the Vaccinated group showed an average daily weight gain that was 12.5 g/day higher than the Control group. The 90% confidence interval for this estimate ranged from a growth that was 6.6 g/day lower to a growth that was 31.5 g/day higher in the Vaccinated group than in the Control group.

Study 2

Design of Study 2

The objective of this study was to assess the efficacy of the same vaccine as used in the first study in finishing pigs under field conditions, but as a one shot vaccine. The study was conducted as a randomised, blinded, saline controlled clinical efficacy trial. About 750 3-4-week-old piglets were allocated randomly within litter to the test or to the control group. The piglets in the test group were vaccinated once intramuscularly with 2 ml of the vaccine and the piglets of the control group were injected with 2 ml of saline. At an age of 10 (±1) weeks, 648 study piglets, 324 from each treatment group, were transported to the finishing farm. From then on, the control pigs were housed in separate pens from the vaccinated pigs in the same unit (8 pens of 8-11 animals per treatment group per unit) until slaughter (at an age of 25 weeks)

A first parameter assessed was the average daily weight gain (ADWG) of the pigs between the different weighings: at admission, after transfer to the finishing farm and just prior to slaughter. A second parameter assessed was *Lawsonia* shedding: after transfer to the finishing farm, at 15 and 20 weeks of age and just prior to slaughter.

Results of Study 2

During this second study, a *Lawsonia* infection went through the herd as evidenced by PCR data on faeces. Only one animal in the control group had slight clinical symptoms (confirmed to be the result of a *Lawsonia* infection, as determined after necropsy). It can thus be confirmed that the group was affected by a subclinical infection resulting from a field exposure to of the (wild type) bacterium.

The effect on ADWG is indicated in Table 5. As can be seen, the average daily weight gain during the nursery period was 319 grams per day in the test group, and 307 grams per day in the control group. The differences in average daily weight gain (ADWG) during the nursery period were significantly different between the control and the test group (ANOVA: p=0.0203). The ADWG in the finishing period, and the overall ADWG was also higher in the test group. Although the differences of 7 gram per day between the control and the test group are commercially relevant (leading to a difference in end weight of approximately 1.4 kg), they were not statistically significant.

TABLE 5

Average daily weight gain (g/day), by vaccination group and period

| | Control group | Test group |
|---|---|---|
| Nursery | 307[a] | 319[b] |
| Finishing | 764[c] | 771[d] |
| Overall | 633[e] | 640[f] |

[ab]Mixed model ANCOVA, p = 0.0203
[cd]Mixed model ANCOVA, p = 0.6356
[ef]Mixed model ANCOVA, p = 0.4229

Regarding *Lawsonia* shedding it appeared that in study week 6 all faecal samples were negative for *Lawsonia intracellularis*. In week 11, seven samples (19%) from the control group and none of the test group were positive. In week 16 seven samples (19%) from the control group and one of the test group were positive. In week 21 all animals were negative again. The number of pens with PCR *Lawsonia* positive faecal samples (for 1 or 2 consecutive weeks) during the study was significantly lower in the test group (Fisher exact test, p<0.001) compared to the control group.

Study 3

Design of Study 3

The primary objective of this study was to further assess the efficacy of the vaccine used in the previous studies under field conditions against bacterial shedding, after a one dose or two dose vaccination scheme. The study was carried out according to a randomised and blinded design on a family farm having a *Lawsonia* infection in its herd. Healthy 3-10-day-old suckling piglets were allocated randomly, within litters, to one of two test groups or a control group (320 animals per group). The piglets in one test group (2×1 ml) were vaccinated with 1 ml of the vaccine at 3-10 days of age and 21 days later this vaccination was repeated. The piglets of the other test group (1×2 ml) were vaccinated with 2 ml of the vaccine at 24-31 days of age. The piglets in the control group were injected with 1 ml of Saline at 3-10 days of age and 21 days later. Faecal samples for *Lawsonia* PCR were taken in weeks 6, 8, 10, 12 and at a weekly basis thereafter until the pigs were slaughtered at the age of 23 weeks.

Results of Study 3

During this second study, a *Lawsonia* infection went through the herd as evidenced by PCR data on faeces. No animals had clinical symptoms of a *Lawsonia* infection.

Thus, the group was affected by a subclinical infection resulting from a field exposure to of the (wild type) bacterium.

Regarding the *Lawsonia* shedding a large difference in occurrence of positive faeces samples was found between the farrowing batches of the control group: in the first farrowing batch positive control samples were found late during finishing (week 18 and 19), in the second batch only in week 21 positive samples were found and in the third batch one positive sample was found in week 21. However, in the fourth batch from week 17 onwards positive samples were detected, while in the fifth batch already in week 14 a positive sample was found. Summarized, 50% of the controls delivered one or more positive samples from week 14 onwards, two (6%) from the 2×1 ml group, and 4 (12%) of the 1×2 ml group was positive. The number of animals with PCR *Lawsonia* positive faecal samples (for 1 or 2 consecutive weeks) during the study was significantly lower in the 1×2 ml group (Fisher's exact test, $p<0.0001$) and 2×1 ml group (Fisher's exact test, $p=0.0002$) compared to the control group.

The invention claimed is:

1. A method to reduce the shedding of *Lawsonia intracellularis* bacteria associated with subclinical infection with *Lawsonia intracellularis* in a pig, by systemic administration of a vaccine comprising non live *Lawsonia intracellularis* antigen and a pharmaceutically acceptable carrier to the pig.

2. The method of claim 1, wherein the method is for preventing shedding of the bacteria.

3. The method of claim 1, wherein the method is also for reducing the negative impact on average daily weight gain (ADWG) of the pig associated with the subclinical infection with *Lawsonia intracellularis*.

4. The method of claim 1, wherein the vaccine is administered only once.

5. The method of claim 1, wherein the vaccine is administered when the pig is 3-10 days of age.

6. The method of claim 1, wherein the non live *Lawsonia intracellularis* antigen comprises the carbohydrates that in live *Lawsonia intracellularis* bacteria are in association with the outer cell membrane of these bacteria.

7. The method of claim 1, wherein the non live *Lawsonia intracellularis* antigen is antigen purified from a composition comprising killed *Lawsonia intracellularis* bacteria.

8. The method of claim 1, wherein the non live *Lawsonia intracellularis* antigen is killed whole cell *Lawsonia intracellularis*.

* * * * *